United States Patent

Faccioli et al.

[11] Patent Number: 6,126,661
[45] Date of Patent: Oct. 3, 2000

[54] INTRAMEDULLARY CAVITY NAIL AND KIT FOR THE TREATMENT OF FRACTURES OF THE HIP

[75] Inventors: Giovanni Faccioli, Monzambano; Daniele Venturini, Povegliano Veronese; Franco Lavini, Verona; Lodovico Renzi Brivio, Verona; Sander Ten Veldhuijs, Verona, all of Italy

[73] Assignee: Orthofix S.R.L., Bussolengo Verona, Italy

[21] Appl. No.: 09/008,943

[22] Filed: Jan. 20, 1998

[30] Foreign Application Priority Data

Jan. 20, 1997 [IT] Italy ................... VR97A0003

[51] Int. Cl.⁷ .................................................. A61B 17/56
[52] U.S. Cl. .................. 606/64; 606/62; 606/96; 606/98
[58] Field of Search .................. 606/62, 64, 67, 606/96, 98, 104, 86

[56] References Cited

U.S. PATENT DOCUMENTS

| | | | |
|---|---|---|---|
| 3,433,220 | 3/1969 | Zickel | 606/67 |
| 4,622,959 | 11/1986 | Marcus . | |
| 4,875,474 | 10/1989 | Border . | |
| 5,035,697 | 7/1991 | Frigg | 606/67 |
| 5,167,663 | 12/1992 | Brumfield | 606/64 |
| 5,176,681 | 1/1993 | Lawes et al. | 606/64 |
| 5,429,640 | 7/1995 | Shuler et al. | 606/64 |
| 5,472,444 | 12/1995 | Huebner et al. | 606/64 |
| 5,536,127 | 7/1996 | Penning | 411/413 |
| 5,562,666 | 10/1996 | Brumfield | 606/64 |
| 5,573,536 | 11/1996 | Grosse et al. | 606/60 |
| 5,653,709 | 8/1997 | Frigg | 606/64 |
| 5,697,930 | 12/1997 | Itoman et al. | 606/64 X |
| 5,713,902 | 2/1998 | Friedl | 606/64 |
| 5,766,174 | 6/1998 | Perry | 606/64 X |
| 5,766,179 | 6/1998 | Faccioli et al. | 606/98 |
| 5,800,440 | 9/1998 | Stead | 606/104 |
| 5,928,235 | 7/1999 | Friedl | 606/64 |
| 5,941,885 | 8/1999 | Jackson | 606/104 |
| 6,027,506 | 2/2000 | Faccioli et al. | 606/98 |

FOREIGN PATENT DOCUMENTS

| | | |
|---|---|---|
| 0355411 | 2/1990 | European Pat. Off. . |
| 0640318 | 3/1995 | European Pat. Off. . |
| 0736286 | 10/1996 | European Pat. Off. . |
| 2713914 | 6/1995 | France . |
| 94/13219 | 6/1994 | WIPO ........... 606/67 |
| 94/27508 | 12/1994 | WIPO ........... 606/67 |
| WO 9517857 | 7/1995 | WIPO . |

OTHER PUBLICATIONS

European Search Report, Application No. EP 97 12 2921, dated Apr. 9, 1998, 4 pages.

*Primary Examiner*—Jeffrey A. Smith
*Attorney, Agent, or Firm*—Hopgood, Calimafde, Kalil & Judlowe, LLP

[57] ABSTRACT

An intramedullary cavity nail for the treatment of proximal femoral fractures, comprises a solid elongate body with a proximal portion (2) having at least one transverse bore for accommodating a corresponding screw (9, 10) for stabilizing the femoral neck, the proximal portion being joined to a distal portion (3) having at least one distal bore (16) for accommodating at least one diaphysis screw for stabilizing the distal part of the femur. The proximal portion (2) has a substantially constant diameter ($\phi_p$) adapted to be stably anchored in a relatively limited length bore of the femur for reducing blood losses, while said distal portion (3) has a substantially constant diameter ($\phi_d$) which is less than that of said proximal portion, for ease of insertion in the medullary canal of the femur without any drilling. The proximal and distal portions (2, 3) are substantially rectilinear and form between themselves a predetermined deviation angle ($\beta$) in a lateral plane. The proximal portion (2) has a pair of inclined bores (7, 8) adapted for accommodating respective cephalic screws (9, 10) for the fixing of the femoral head.

A template (20) with provision for angularly keyed engagement to the proximal end of the nail, has alignment bores for stabilized guidance of drill bits with each of the respective transverse bores of the intramedullary nail.

19 Claims, 4 Drawing Sheets

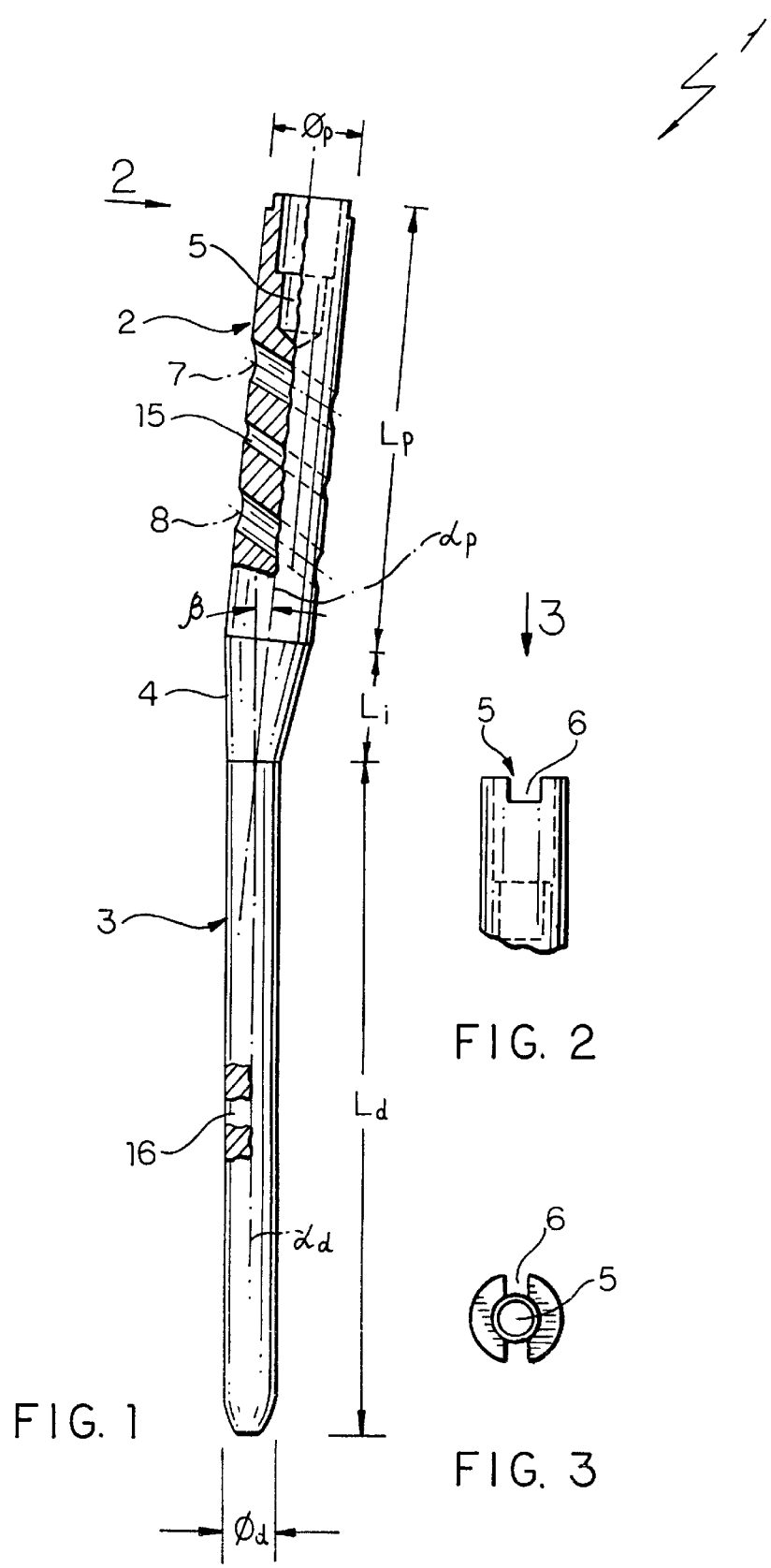

INTRAMEDULLARY CAVITY NAIL AND KIT FOR THE TREATMENT OF FRACTURES OF THE HIP

TECHNICAL FIELD

The present invention relates to an intramedullary cavity nail for the treatment of proximal femoral fractures of the type comprising a solid elongate body having a proximal portion with at least one hole for accommodating corresponding screws for stabilization of the femoral neck, united to a distal portion with at least one distal hole for accommodating at least one diaphysis screw for stabilization of the distal part of the femur.

The invention also concerns an instrument for the installation of the nail in the medullary canal of the femur.

BACKGROUND ART

It is known that among geriatric patients pertrochanteric fractures are the most frequent in connection with those of the region of the neck of the bone. In fact, the advanced age and the pathologies which are encountered in these patients make necessary a timely stabilization of skeletal injuries in order to reduce to a minimum the bed confinement and the rehabilitation times by means of interventions which are less sanguinary and invasive as possible. In fact, it is necessary to avoid the complications brought about by the so-called immobilization syndrome, which may be lethal for patients in delicate metabolical compensation; and it is necessary to reduce to a minimum blood losses related to surgical intervention.

At the same time, the syntheses means utilized must be stable in order to allow the patient to very timely assume a seated position and, two or three days following the intervention, to reassume an erect posture with progressive weight.

A known technique for the consolidation of intertrochanteric, pertrochanteric, and subtrochanteric fractures of the femur involves the use of tubular intramedullary cavity nails with a proximal portion bent by some degrees in a medial-lateral plane with respect to a smaller diameter diaphysis portion in order to adapt to the physiological curvature of the femur. Sometimes, the curvature is present in two mutually orthogonal planes in order to favor further adaptation to the medullary cavity of the bone.

The known tubular nails are generally fixed by means of two diaphysis nails in order to block the rotation of the nail and one or two cephalic screws for compressing the spongy tissue in the focus fracture.

A first drawback of known intramedullary cavity nails of the above-described type resides in the fact that they have both a proximal part and a distal part of relatively elevated diameter, generally greater than 10-mm, and therefore their installation requires complex drilling of the bone for the entire length of the nail and can provoke internal stresses of the bone.

Moreover, the diaphysis screws are rather close to the distal end of the nail and can provoke stress concentrations and rupture of the femur at the base of the nail.

Finally, the cephalic screws are normally mutually parallel and therefore the head can be subject to slipping, with consequent loss of stability of the fracture.

BRIEF STATEMENT OF THE INVENTION

A principal aim of the present invention is to eliminate or at least reduce the above-described drawbacks by providing an intramedullary cavity nail which has characteristics of elevated strength, reliability and biocompatibility, and which is minimally invasive.

A particular aim is to provide an intramedullary cavity nail which requires minimum bone-drilling operations and skin incisions, thereby to limit blood loss and operating intervention and rehabilitation times.

A further aim is to provide an intramedullary cavity nail of elevated biocompatibility and of reduced cost.

Another further aim is to provide an intramedullary cavity nail which is easily installable in the medullary canal, using an extremely simplified and effective instrument.

In accordance with one preferred aspect of the invention, an intramedullary cavity nail of the indicated type is characterized by the fact that said proximal portion has a substantially constant diameter that is adapted to be stably anchored in a relatively limited-length bore of the femur, thereby reducing blood loss, while said distal portion has a substantially constant diameter smaller than that of said proximal portion, such that the distal portion can be easily inserted in the medullary canal of the femur, without drilling to accommodate the distal portion.

BRIEF DESCRIPTION OF DRAWINGS

The particular characteristics and advantages of the invention will become apparent from the description of some preferred but not exclusive embodiments of the intramedullary cavity nail according to the invention, shown in the accompanying drawings. In said drawings:

FIG. 1 is a lateral elevation view of an intramedullary cavity nail according to a preferred aspect of the invention;

FIG. 2 is a fragmentary view in elevation, for a detail of the nail of FIG. 1, as seen from the aspect of arrow II in FIG. 1;

FIG. 3 is an end view of the detail of FIG. 2, as seen from the aspect of arrow III in FIG. 2;

DETAILED DESCRIPTION

Figure 4:
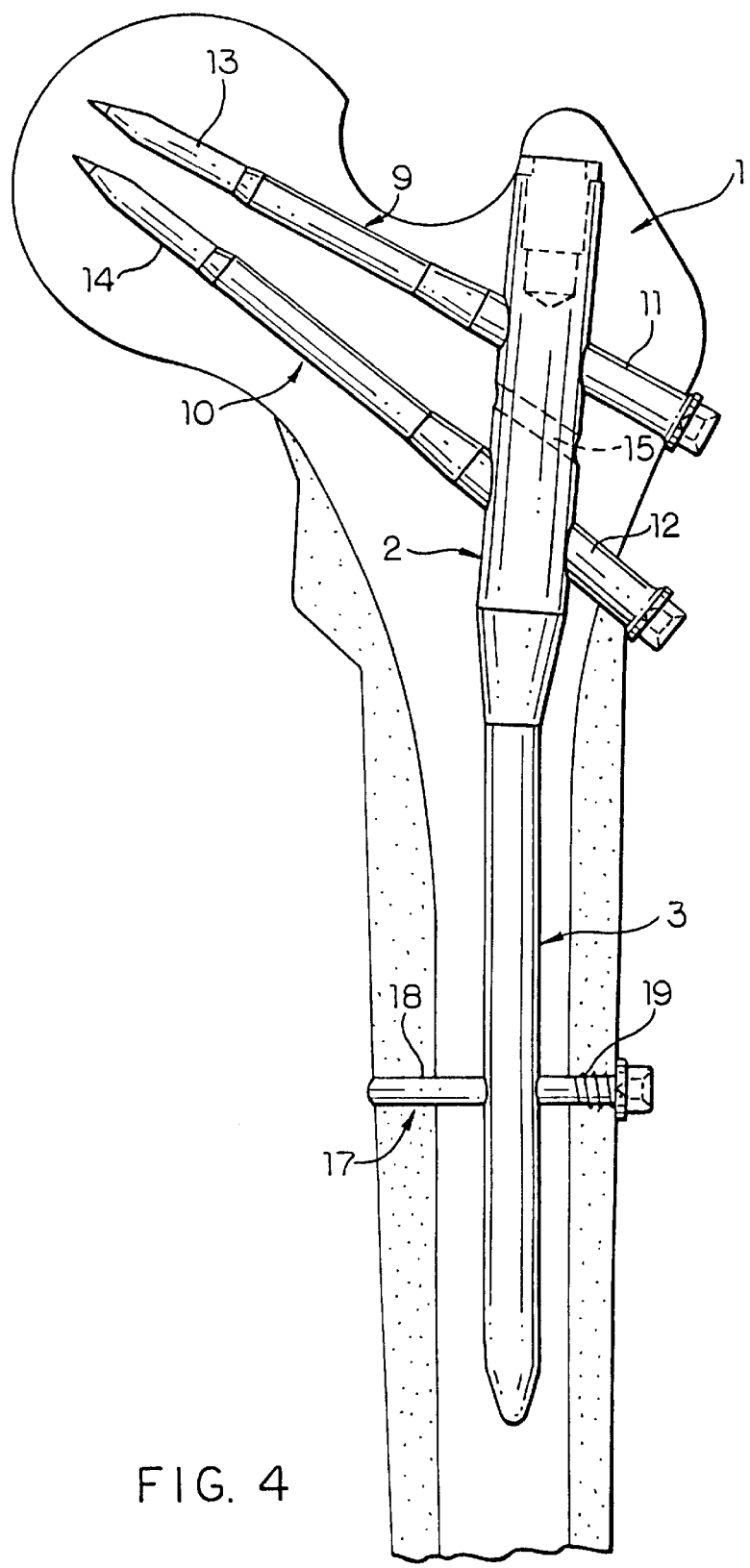
FIG. 4 is a lateral elevation view of the intramedullary cavity nail of FIG. 1, inserted in the medullary canal of a femur.

In the drawings, an intramedullary cavity nail according to a preferred aspect of the invention is designated generally by reference numeral 1. Generally speaking, the nail 1 comprises a solid elongate body of biocompatible metal, for example titanium or stainless steel of the type AISI316KVM, essentially formed by a proximal portion 2, united to a distal portion 3, by means of a substantially truncated-conical intermediate portion 4 having a length $L_i$.

Both of the portions 2, 3 are substantially rectilinear and their axes form between them a relatively small deviation angle $\beta$, for example, an included angle between 4° and 5°. The deviation angle $\beta$ may also be in the range between 3° and 10°.

The proximal portion 2, having a length $L_p$, for example between 70-mm and 80-mm, has a substantially constant and relatively large average diameter $\phi_p$, which may for example be in the range between 12-mm and 16-mm, and preferably of about 14-mm, thus rendering the proximal portion 2 adaptable for stable anchorage in a hole bored in a trochanteric zone of limited length of the bone. In this manner, one obtains a reduction of blood loss during the operation of tissue incision and a simplification of the surgical intervention, with greater chances of success.

Toward the free end of the proximal portion 2, a threaded seat 5 is formed, with an end edge that has a diametrical notch 6.

In the proximal portion 2 and below seat 5, at least two spaced transverse bores 7, 8 are provided for cephalic screws 9, 10, for stabilizing the femoral head; bores 7, 8 are inclined with respect to the axis $\alpha_p$ of the proximal portion 2. Suitably, the bores 7, 8 are inclined with respect to the axis of the proximal portion 2 at an average angle of about 115°, and they may be inclined with respect to each other by about 10° so as to be convergent, in order to prevent a shifting of the head and/or the exit of screws 9, 10 therefrom.

Preferably, the cephalic screws 9, 10 have respective proximal end portions 11, 12 with possibly but not necessarily increased diameter, stably engageable in the bores 7, 8 of the proximal portion 2; and distal end portions 13, 14 of screws 9, 10 may be of lesser or equal diameter, and with self-threading tips for engagement into the femoral head. The cephalic screws 9, 10 may have respective maximum diameter portions 11, 12 for the accommodation in corresponding bores 7, 8 of the proximal portion 2, with a maximum diameter in the range between 3-mm and 8-mm, and particularly 7-mm.

In certain cases, the proximal portion 2 may be provided with a third bore 15, inclined by an average angle of for example about 115° with respect to the axis $\alpha_p$ for a medial Kirschner wire substantially coaxial with the femoral head; such a wire will be understood to be of smaller diameter than the two screws, and is not shown in the drawings.

The distal portion 3, having a length $L_d$, for example in the range between 100-mm and 120-mm, has an average diameter $\phi_d$ less than diameter $\phi_p$ of the proximal portion, for example in the range between 8-mm and 10-mm and preferably about 9-mm, thus rendering the distal portion 3 adaptable for easy insertion in the medullary canal of the femur without any boring of the same. The diameter $\phi_d$ may also be in the range of between 7-mm and 11-mm.

In the distal portion 3, a single transverse bore 16 is provided, substantially perpendicular to the axis $\alpha_d$, for diaphysis stabilization and a torsional locking pin 17. The bore 16 is preferably provided at about midway of the length $L_d$ so as to position the locking pin 17 at insufficient axial offset from the free tip of the distal portion 3, thereby reducing any risk of breakage of its end portion.

Preferably, the diaphysis locking pin 17 has a smooth shank portion 18 of substantially constant diameter stably engageable in the bore 16 and a threaded proximal-end portion 19 engageable in the spongy tissue of the bone.

With the described configuration, and as shown in FIG. 4, the nail 1 allows for an optimally stabilized installation and a stable and quick synthesis of the bone, with a reduced invasive technique and with limited blood loss.

Both the cephalic screws and the diaphysis pin are preferably made with the same materials as the nail for reasons of biocompatibility.

According to a further aspect of the invention, there is provided an instrument (FIG. 8) for positioning the above-described intramedullary cavity nail and for performing the necessary drilling of the bone.

Advantageously, such an instrument comprises a drilling template 20 which extends in the principal plane defined by nail axes $\alpha_p$ and $\alpha_d$. As shown, template 20 is an outrigger having a hand grip 21 for grasp by the surgeon, and an offsetting transverse arm 22 has an end bore 23 for connection to the proximal end of nail 1, on the axis $\alpha_p$. A guide sleeve 24 is keyed in the bore 23 having diametrical protrusions or keying teeth 25 at its lower end; teeth 25 will be understood to be in the principal plane of development of the template and to be engageable in the diametrical notch 6 of the seat 5 of nail 1, in order to guarantee template 21 alignment during the surgical intervention.

A pin 26 (FIG. 8) having a manually operable knob 27 extends through the bore of sleeve 24 and has a threaded end 28 for engagement with the threaded seat 5 of the intramedullary nail 1 in order to guarantee its connection with the template 20.

Figure 8:
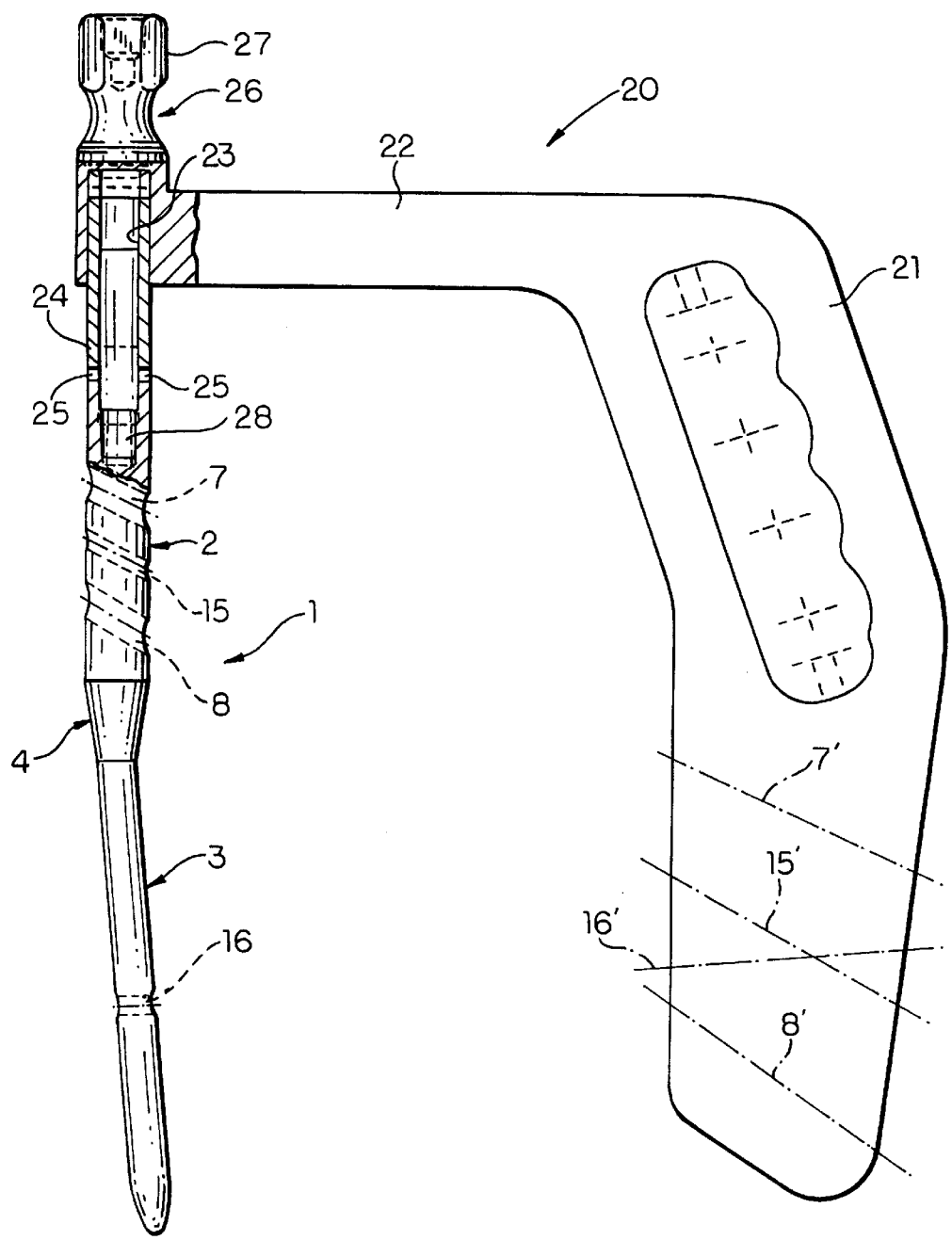
FIG. 8 is a general lateral elevation view of the intramedullary cavity nail of FIG. 1, coupled to an instrument for use in installing the nail in a medullary canal.

The lower part of the grip 21 of template 20 is seen in FIG. 8 to be provided with guide bores (suggested only by their axes 7', 8', 15', 16') for bone-drill bits, in correspondence with the bores 7, 8, 15 and 16 of the nail.

In use, the surgeon performs the drilling of the trochanteric zone of the medullary canal of the femur for about 10-cm, whereafter the nail is inserted, taking care that the notch 6 along the edge of its threaded seat is positioned in a lateral plane of the limb. Thereafter the nail is connected to the drilling template 20 taking care that the protrusions of keying teeth 25 of guide sleeve 24 of the latter are engaged in the notch 6 of nail 1. Finally, pin 26 is inserted in the sleeve 24 and its threaded end 28 is driven into the threaded seat 5 of the pin, thereby providing its stable connection. At this point, bone-drilling may be initiated via guide bores 7', 8', 15', 16', corresponding to and aligned with the bores 7, 8, 15, 16 of the intramedullary nail. Finally, screws 9, 10, 17 may be inserted in the respective bores for providing stabilization of the femur in a rapid and secure manner.

Figure 5:
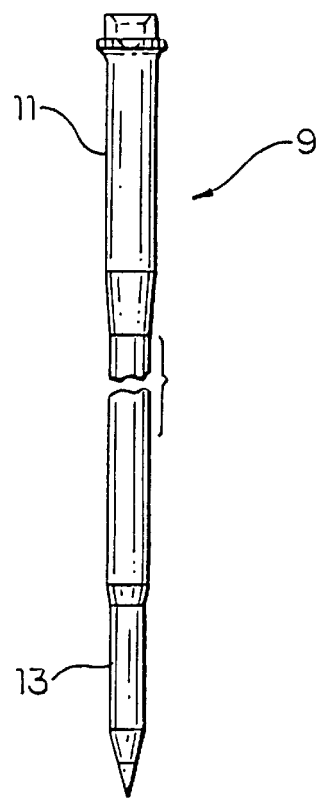
FIG. 5 is a lateral elevation view of a cephalic screw used in fixing the installed nail of FIG. 4.
Figure 6:
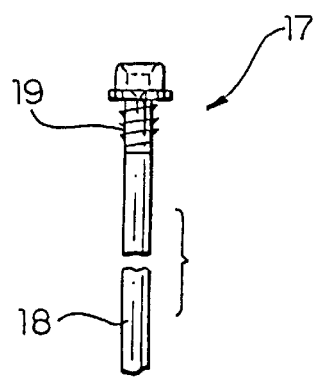
FIG. 6 is a lateral elevation view of a diaphysis screw or pin used in fixing the installed nail of FIG. 4.
Figure 7:
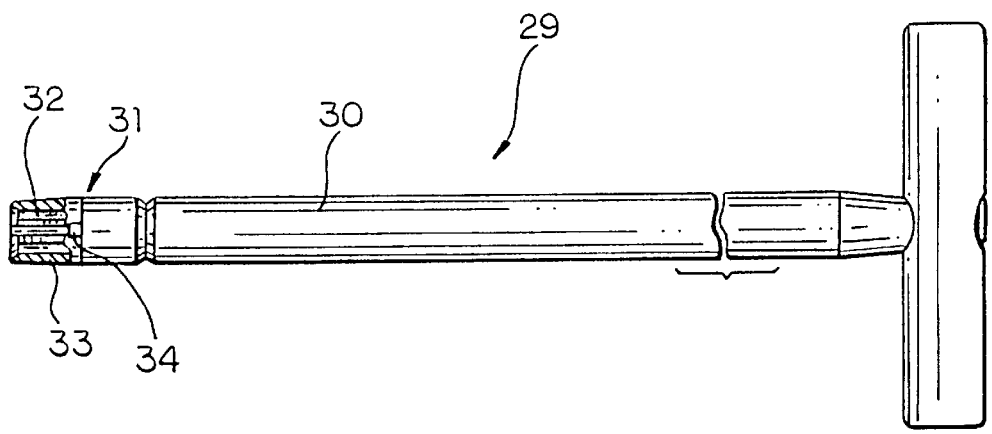
FIG. 7 is a lateral elevation view of a part of a tool according to a preferred aspect of the invention for use in manipulating screws of FIGS. 5 and 6, to secure the installed nail to the bone in FIG. 4.

For the insertion and stabilization of such screws while avoiding accidentally dropping them, it is possible to utilize a particular T-shaped tool, illustrated clearly in FIG. 7 and generally indicated by the reference numeral 29. The tool has an elongate stem 30 with a head 31 having a socket formation 32 of hexagonal section, to fit the hexagonal head of a screw (e.g., as in FIG. 5 or FIG. 6) and a lateral gripping means, an embodiment of which is an external tubular portion 33 with a diametrical longitudinal notch 34 for forming two semicylindrical elastic wings which can grip the head of the screw, against accidental loss of screw head/socket engagement in the course of tool manipulation.

What is claimed is:

1. Intramedullary cavity nail for the treatment of femoral fractures, comprising a solid elongate body having a proximal portion (2) with at least one transverse bore for accommodating at least one corresponding screw (9, 10) for stabilizing the femoral neck, joined to a distal portion (3) with at least one distal transverse bore (16) for accommodating at least one diaphysis screw (17) for stabilizing the distal part of the femur, characterized by the fact that said proximal portion (2) has a substantially constant diameter ($\phi_p$) adapted to be stably anchored in a relatively limited length bore of the femur for reducing blood losses, while said distal portion (3) has a substantially constant diameter ($\phi_d$) which is less than that of said proximal portion (2) for ease of insertion without drilling in the medullary canal of the femur, wherein said proximal and distal portions (2, 3) are substantially rectilinear and form between themselves a predetermined deviation angle (β) in a lateral plane.

2. Intramedullary cavity nail according to claim 1, wherein said angle of deviation (β) is in the range between 3° and 10°.

3. Intramedullary cavity nail according to claim 1, wherein said angle of deviation (β) is about 5°.

4. Intramedullary cavity nail according to claim 1, wherein the diameter ($\phi_p$) of said proximal portion (2) is in the range between 12-mm and 16-mm.

5. Intramedullary cavity nail according to claim 1, wherein the diameter ($\phi_p$) of said proximal portion (2) is about 14-mm.

6. Intramedullary cavity nail according to claim 1, wherein the diameter ($\phi_d$) of said distal portion (3) is in the range between 7-mm and 11-mm.

7. Intramedullary cavity nail according to claim 1, wherein the diameter ($\phi_d$) of said distal portion (3) is about 9-mm.

8. Intramedullary cavity nail for the treatment of femoral fractures, comprising a solid elongate body having a proximal portion (2) with at least one transverse bore for accommodating at least one corresponding screw (9, 10) for stabilizing the femoral neck, joined to a distal portion (3) with at least one distal transverse bore (16) for accommodating at least one diaphysis screw (17) for stabilizing the distal part of the femur, characterized by the fact that said proximal portion (2) has a substantially constant diameter ($\phi_p$) adapted to be stably anchored in a relatively limited length bore of the femur for reducing blood losses, while said distal portion (3) has a substantially constant diameter ($\phi_d$) which is less than that of said proximal portion (2) for ease of insertion without drilling in the medullary canal of the femur, wherein said proximal portion (2) has at least two axially spaced transverse bores (7, 8) which are inclined to the axis ($\alpha_p$) of said proximal portion (2), and which are adapted for accommodating respective cephalic screws (9, 10) for fixation in the femoral head.

9. Intramedullary cavity nail according to claim 8, wherein said cephalic screws (9, 10) have a notably smaller diameter than that of said proximal portion (2) and are slightly convergent with respect to one another and with respect to the median axis of the femoral head in order to exert on the latter a reaction force with a longitudinal component to resist shifting and/or axial penetration.

10. Intramedullary cavity nail according to claim 9, wherein said cephalic screws (9, 10) have respective maximum diameter portions (11, 12) for the accommodation in corresponding bores (7, 8) of said proximal portion (2), with a maximum diameter in the range between 3-mm and 8-mm.

11. Intramedullary cavity nail according to claim 10, wherein said maximum diameter is about 7-mm.

12. Intramedullary cavity nail for the treatment of femoral fractures, comprising a solid elongate body having a proximal portion (2) with at least one transverse bore for accommodating at least one corresponding screw (9, 10) for stabilizing the femoral neck, joined to a distal portion (3) with at least one distal transverse bore (16) for accommodating at least one diaphysis screw (17) for stabilizing the distal part of the femur, characterized by the fact that said proximal portion (2) has a substantially constant diameter ($\phi_p$) adapted to be stably anchored in a relatively limited length bore of the femur for reducing blood losses, while said distal portion (3) has a substantially constant diameter ($\phi_d$) which is less than that of said proximal portion (2) for ease of insertion without drilling in the medullary canal of the femur, wherein a single diaphysis screw (17) for counteracting torsional stresses of the nail is accommodated in a single bore (16) substantially perpendicular to the axis ($\alpha_d$) of the distal portion (3) at a location of axial offset from said proximal portion (2).

13. Intramedullary cavity nail according to claim 12, where in said diaphysis screw (17) has (i) a substantially constant diameter principal portion (18) corresponding to that of said single bore (16) of said distal portion, and (ii) a threaded portion (19) of larger diameter than that of said principal portion.

14. Intramedullary cavity nail according to claim 13, wherein said diaphysis screw (17) is positioned approximately midway along the length ($L_d$) of said distal portion, thereby reducing risk of breakage of the nail toward its free end.

15. Intramedullary cavity nail for the treatment of femoral fractures, comprising a solid elongate body having a proximal portion (2) with at least one transverse bore for accommodating at least one corresponding screw (9, 10) for stabilizing the femoral neck, coined to a distal portion (3) with at least one distal transverse bore (16) for accommodating at least one diaphysis screw (17) for stabilizing the distal part of the femur, characterized by the fact that said proximal portion (2) has a substantially constant diameter ($\phi_p$) adapted to be stably anchored in a relatively limited length bore of the femur for reducing blood losses, while said distal portion (3) has a substantially constant diameter ($\phi_d$) which is less than that of said proximal portion (2) for ease of insertion without drilling in the medullary canal of the femur, wherein said proximal portion (2) has, near its free end, a threaded seat (5) for a connection pin (26) for connection to a drilling template (20) arranged in the principal plane of the nail.

16. Intramedullary cavity nail according to claim 15, wherein the edge of said threaded seat (5) has a diametrical notch (6) coplanar with the principal plane of the nail for keyed reception of alignment protrusions (25) between the nail and the template (20).

17. A kit comprising an intramedullary cavity nail according to claim 15, and a drilling template (20) having a grip (21) with a radially offsetting arm (22) having at its free end an axial bore (23) for guided passage of said connection pin (26).

18. A kit nail according to claim 17, wherein said grip (21) has a series of guide bores for drilling bits, alignable with the bores (7, 8, 15) of cephalic and diaphysis screws in the bone-drilling phase of installing the intramedullary nail.

19. A kit according to claim 17, and further comprising a special tool (29) for use in assembling said template to the nail comprising a longitudinal stem (30) having a head (31) with a bolt-engageable socket (32) and with lateral gripping means (33) adapted to engage the head of a bolt for avoiding an accidental loss of tool engagement.

* * * * *